United States Patent
Chen et al.

(10) Patent No.: US 9,771,318 B2
(45) Date of Patent: Sep. 26, 2017

(54) ETHOXYLATE ISOCYANATE COMPOUND AND ITS USE AS A EMULSIFIER

(71) Applicants: Dow Global Technologies LLC, Midland, MI (US); Rohm and Haas Company, Philadelphia, PA (US)

(72) Inventors: Yongchun Chen, Shanghai (CN); Shiling Zhang, Shanghai (CN); Ling Yuan, Shanghai (CN); Guoling Hou, Shanghai (CN)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 176 days.

(21) Appl. No.: 14/436,993

(22) PCT Filed: Oct. 28, 2013

(86) PCT No.: PCT/CN2013/086024
§ 371 (c)(1),
(2) Date: Apr. 20, 2015

(87) PCT Pub. No.: WO2014/067430
PCT Pub. Date: May 8, 2014

(65) Prior Publication Data
US 2015/0274649 A1    Oct. 1, 2015

(30) Foreign Application Priority Data
Oct. 29, 2012 (CN) .......................... 2012 1 0421466

(51) Int. Cl.
| | | |
|---|---|---|
| *B01F 17/00* | (2006.01) | |
| *C07C 271/20* | (2006.01) | |
| *C08G 18/02* | (2006.01) | |
| *C08G 18/10* | (2006.01) | |
| *C08G 18/28* | (2006.01) | |
| *C08G 18/70* | (2006.01) | |
| *C08G 18/79* | (2006.01) | |

(52) U.S. Cl.
CPC .......... *C07C 271/20* (2013.01); *B01F 17/005* (2013.01); *C08G 18/02* (2013.01); *C08G 18/10* (2013.01); *C08G 18/283* (2013.01); *C08G 18/706* (2013.01); *C08G 18/792* (2013.01)

(58) Field of Classification Search
CPC ... B01F 17/005; C07C 271/20; C08G 18/283; C08G 18/706; C08G 18/792; C08G 18/02; C08G 18/10
See application file for complete search history.

(56) References Cited

U.S. PATENT DOCUMENTS

| | | |
|---|---|---|
| 4,303,774 A | 12/1981 | Nachtkamp et al. |
| 4,663,377 A | 5/1987 | Hombach et al. |
| 5,252,696 A | 10/1993 | Laas et al. |
| 5,468,804 A | 11/1995 | Schmalstieg et al. |
| 6,492,456 B1 | 12/2002 | Revelant |
| 7,553,902 B2 * | 6/2009 | Haeberle .............. C08G 18/283 156/330.9 |
| 2004/0019160 A1 | 1/2004 | Dai et al. |
| 2005/0222368 A1 | 10/2005 | Reiners |
| 2007/0270508 A1 | 11/2007 | Liu |
| 2008/0103263 A1 | 5/2008 | Erdem et al. |
| 2008/0132638 A1 * | 6/2008 | Huybrechts ........ C08G 18/0828 524/608 |
| 2010/0324199 A1 | 12/2010 | Fickers et al. |

FOREIGN PATENT DOCUMENTS

WO    2006029140 A1    3/2006

OTHER PUBLICATIONS

Meier-Westhues, "Polyurethanes-Coatings, Adhesives, and Sealants," Vincent Network (2007).
Shaoxiong, et al., "Polyurethane resin and its application," Chemical Industry Press, pp. 597-601 (2002).

* cited by examiner

*Primary Examiner* — Patrick Niland
(74) *Attorney, Agent, or Firm* — Carl P. Hemenway

(57) ABSTRACT

Provided is a composition comprising one or more compound having the structure of formula II:

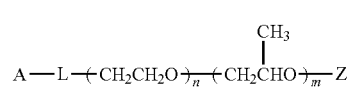

wherein
A is a residue of a polyisocyanate,
L is a linking group formed by a reaction of an isocyanate group with an isocyanate-reactive group,
n is 5 to 25,
m is 0 to 100, and
Z is methyl or ethyl or propyl, and
wherein the ratio of the sum of the moles of isocyanate groups plus the moles of said L groups to the moles of said Z groups is 2:1 to 30:1.
Also provided is an emulsion in which the particles comprise such a composition and further comprise one or more water-insoluble compound that does not have the structure A-NCO.

9 Claims, No Drawings

ETHOXYLATE ISOCYANATE COMPOUND AND ITS USE AS A EMULSIFIER

It is often desirable to provide a water-insoluble compound in a waterborne composition. One possible approach to this goal is to attempt to form an emulsion of droplets in water, where the droplets contain the water-insoluble compound and where those droplets are stabilized by an emulsifier. In such an emulsion, it is sometimes also desirable that the emulsifier is reactive and capable of acting as a crosslinker U.S. Pat. No. 4,663,377 describes a preparation that contains an aliphatic polyisocyanate and an emulsifier.

It is desired to provide a compound that has one or more isocyanate groups and that is capable of acting as an emulsifier for stabilizing emulsions of water-insoluble compounds. Also desired are emulsions made of such water-insoluble compounds and such emulsifiers. It is further desired to provide a compound that has two or more isocyanate groups and that is capable of acting as an emulsifier for stabilizing emulsions of water-insoluble aromatic polyisocyanates. Also desired are emulsions made of such aromatic polyisocyanates and such emulsifiers.

The following is a statement of the invention.

The first aspect of the present invention is a composition comprising one or more compound having the structure of formula II:

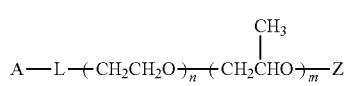

II wherein
  A is a residue of a polyisocyanate,
  L is a linking group formed by a reaction of an isocyanate group with an isocyanate-reactive group,
  n is 5 to 25,
  m is 0 to 100, and
  Z is methyl or ethyl or propyl, and
wherein the ratio of the sum of the moles of isocyanate groups plus the moles of said L groups to the moles of said Z groups is 2:1 to 30:1.

The second aspect of the present invention is an emulsion comprising particles suspended in an aqueous medium, wherein said particles comprise
  (b) one or more compound having the structure of formula II:

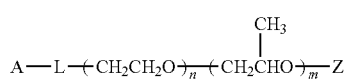

II and
  (c) one or more water-insoluble compound that does not have the structure A-NCO,
wherein
A is a residue of a polyisocyanate, the meaning of A is the same in (b) and (c),
L is a linking group formed by a reaction of an isocyanate group with an isocyanate-reactive group,
n is 5 to 25,
m is 0 to 100, and
Z is methyl or ethyl or propyl, and
wherein the ratio of the sum of the moles of isocyanate groups plus the moles of said L groups to the moles of said Z groups is 2:1 to 30:1.

The following is a detailed description of the invention.

As used herein, the following terms have the designated definitions, unless the context clearly indicates otherwise.

The isocyanate group is —NCO. A polyisocyanate is a compound having two or more isocyanate groups. Some polyisocyanates are polymers and some are not. A diisocyanate is a compound that has exactly two isocyanate groups. The structure of a diisocyanate is OCN—R—NCO, where R is any organic group, which may be substituted or unsubstituted. If R is aliphatic, the diisocyanate is an aliphatic diisocyanate. If R contains any aromatic ring, the diisocyanate is an aromatic diisocyanate.

A dimer of a diisocyanate has the structure VI:

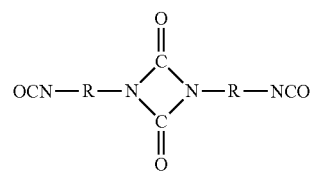

VI

Because structure VI is the dimer of a diisocyanate, the R groups in structure VI are identical to each other. A diisocyanate that is not a dimer of any diisocyanate is known herein as a monomer of a diisocyanate.

A trimer of a diisocyanate has the structure III:

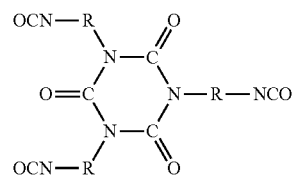

III

Because structure III is the trimer of a diisocyanate, the R groups in structure III are identical to each other.

As used herein, a "residue" of a polyisocyanate is what remains of the structure of that polyisocyanate when a single isocyanate group is disregarded. A polyisocyanate has the structure A-NCO, where A is the residue of the polyisocyanate. The residue of a polyisocyanate has at least one isocyanate group. For Example, structure III may be redrawn to have the structure AT-NCO, where AT is the residue of the trimer of a diisocyanate. In this example, AT has two isocyanate groups.

As used herein, an isocyanate-reactive group is a group that is capable of reacting with an isocyanate group. A linking group is the group formed when an isocyanate group reacts with an isocyanate-reactive group. For example, when an isocyanate group reacts with a hydroxyl group or with an amine group, the resulting linking group is a urethane group or a urea group, respectively. The urethane group has structure IV:

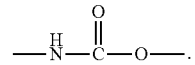

IV

As used herein, an epoxy compound is a compound having one or more epoxy group. A polyepoxy compound is a compound having two or more epoxy groups. A polyepoxy compound may or may not be a polymer.

As used herein a crosslinker is a compound that has two or more reactive groups and that is capable of reacting with reactive groups attached to polymer chains to form crosslinks between polymer chains. The reactive groups on the crosslinker may be the same as or different from the reactive groups attached to the polymer chains.

An aqueous medium is a continuous medium that contains 50% or more water by weight based on the weight of the continuous medium. As used herein, an emulsion is a dispersion of particles distributed through an aqueous medium. The particles in an emulsion may have weight-average particle diameter of 10 nm to 10 micrometer. Weight-average particle diameter herein is known as D50.

A compound is considered herein to be water-insoluble if the maximum amount of that compound that can dissolve in 100 g of water at 25° C. is 0.5 grams.

As used herein, the statement that a ratio is X:1 or higher means that the ratio is Y:1, where Y is equal to or greater than X. Similarly, the statement that a ratio is Z:1 or lower means that the ratio is W:1, where W is equal to or less than Z.

The composition of the present invention preferably contains a polyisocyanate, herein refereed to as "polyisocyanate (a)." Polyisocyanate (a) has the structure I:

A-NCO    I where A is the residue of polyisocyanate (a). Preferably, polyisocyanate (a) is a monomer of a diisocyanate, a dimer of a diisocyanate, or a trimer of a diisocyanate. More preferably, polyisocyanate (a) is a trimer of a diisocyanate.

Certain diisocyanates are preferred for use in polyisocyanate (a). The same diisocyanates are preferred whether used as a monomer of a diisocyanate or as the building blocks for a dimer of a polyisocyanate or a trimer of a polyisocyanate. Preferred diisocyanates for use in polyisocyanate (a) are aliphatic diisocyanates. More preferred are 1,6 hexamethylene diisocyanate (HDI), 1-isocyanato-3-isocyanatomethyl-3,5,5-trimethyl-cyclohexane (IPDI), 4,4'-diisocyanato dicyclohexylmethane (H$_{12}$MDI), and di-isocyanatomethyl-cyclohexane (ADI). More preferred are HDI and ADI; most preferred is HDI.

In preferred embodiments, polyisocyanate (a) is a trimer of a diisocyanate (herein called "trimer (a)") having structure III. Trimer (a) has the structure I:

AT-NCO    I

In trimer (a), residue AT- has the structure V:

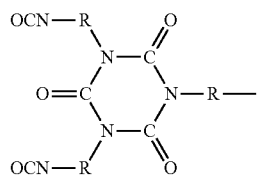

The diisocyanate of which trimer (a) is the trimer is known herein as "diisocyanate (a)."

The composition of the present invention contains a compound (herein called "compound (b)") having structure II:

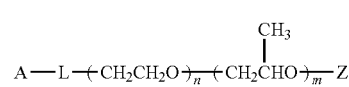

where A in structure II is a residue of a polyisocyanate. When a polyisocyanate (a) is present, A in structure II is identical to A in structure I; L is a linking group formed by a reaction of an isocyanate group with an isocyanate-reactive group, n is 5 to 50, m is 0 to 100, and Z is methyl or ethyl or propyl.

Preferably, L is a urea group or a urethane group. More preferably, L is a urethane group. Preferably, n is 7 or more; more preferably 10 or more. Preferably, n is 45 or less; more preferably 25 or less. Preferably, m is 50 or less; more preferably 10 or less; more preferably 2 or less; more preferably zero. Preferably, Z is methyl.

When polyisocyanate (a) is HDI, it is preferred that n is 7 or more; more preferably 10 or more. When polyisocyanate (a) is HDI, it is preferred that n is 25 or less.

When polyisocyanate (a) is ADI, it is preferred that n is 10 or more; more preferably 14 or more. When polyisocyanate (a) is HDI, it is preferred that n is 18 or less; more preferably 14 or less.

The composition of the present invention comprises a mixture of polyisocyanate (a) and compound (b). This mixture may be characterized by a ratio M-ISO:M-Z. As used herein M-ISO is the sum of the moles of NCO groups plus the moles of L groups. M-Z is the moles of Z groups.

The ratio M-ISO:M-Z may be illustrated by an example. In some embodiments, the composition of the present invention is made by a process that includes a chemical reaction between a polyisocyanate (a) and a compound having structure HO—(CH$_2$CH$_2$O)$_n$—CH3. In such embodiments, an NCO group on trimer (a) reacts with the OH group on the other compound. When contemplating such a chemical reaction, it is useful to characterize reactants prior to the chemical reaction by examining the ratio (herein called the NCO:OH ratio) of the moles of NCO groups on the trimer (a) to the moles of OH groups on the other compound. In this example, the moles of Z groups is the moles of methyl groups, which is the same as the moles of OH groups. In this example, during the chemical reaction, some or all of the NCO groups will react with some or all of the OH groups, and so some or all of the NCO groups will be converted into urethane groups (the L groups in this example). The quantity M-ISO will be the same as the number of moles of NCO groups present in the reactants prior to the chemical reaction. The ratio M-ISO:M-Z of the products after the chemical reaction is the same as the ratio NCO:OH of the reactants prior to the reaction.

M-ISO:M-Z is 2:1 or higher; preferably 4:1 or higher; more preferably 5:1 or higher; more preferably 6:1 or higher. M-ISO:M-Z is 30:1 or lower; preferably 20:1 or lower: more preferably 14:1 or lower; more preferably 10:1 or lower; more preferably 8:1 or lower.

In some embodiments, a composition of the first aspect of the present invention contains some solvent. A solvent is a liquid at 25° C. that does not react with the other ingredients of the composition at 25° C. and that forms a solution with the other ingredients of the composition. When a solvent is present, preferred solvents are alkyl ketones, alkyl ethers, and alkyl acetates. Preferably, if a solvent is present, the amount of solvent is, by weight based on the weight of the composition, 60% or less; more preferably 40% or less.

When polyisocyanate (a) is HDI, the preferred amount of solvent is, by weight based on the weight of the composition, 1% or less; more preferably 0%.

When polyisocyanate (a) is ADI, the preferred amount of solvent is, by weight based on the weight of the composition, 60% or less; more preferably 40% or less. When polyisocyanate (a) is ADI, the preferred amount of solvent is, by weight based on the weight of the composition, 10% or more; more preferably 20% or more.

Some aspects of the present invention involve an emulsion that contains particles suspended in an aqueous medium. The particles contain trimer (a), compound (b), and an additional compound (herein called "compound (c)"). Compound (c) is water-insoluble and is different from both polyisocyanate (a) and compound (b).

While the present invention is not limited to any specific mechanism, it is contemplated that compound (c) and polyisocyanate (a) form a mixture in the interior of each particle and that compound (b) resides at the interface between the particle and the aqueous medium. It is contemplated that compound (c) acts as emulsifier to form and stabilize the particles.

Preferably, compound (c) is a crosslinker. More preferably, compound (c) is a polyepoxy compound or a polyisocyanate. More preferably, compound (c) is a polyisocyanate. For compound (c), preferred aliphatic polyisocyanates are HDI, IPDI, $H_{12}$MDI, ADI, isomers thereof, polymers thereof, and mixtures thereof. Compound (c) preferably is an aromatic polyisocyanate. For compound (c), preferred aromatic polyisocyanates are toluylene-2,4-diisocyanate (2,4-TDI), toluylene-2,6-diisocyanate (2,6-TDI), naphthylene-1,5-diisocyanate, diphenylmethane-4,4'-diisocyanate (MDI), isomers thereof, polymers thereof, and mixtures thereof. More preferred are 4,4'-MDI; 2,4'-MDI; and mixtures thereof.

Preferably the D50 of the particles is 10 nm or larger; more preferably 50 nm or larger. Preferably, the particles have D50 of 2,000 nm or smaller; more preferably 1,000 nm or smaller; more preferably 500 nm or smaller.

Preferably, the emulsion is stable. A stable emulsion does not show any phase separation, settling, floatation, or aggregation upon storage at 25° C. Preferably, the emulsion is stable for 2 hours or more; more preferably 5 hours or more; more preferably 10 hours or more.

In the emulsion of the present invention, it is useful to characterize the sum of the weight of polyisocyanate (a) plus the weight of compound (b) plus the weight of compound (c). This sum may be expressed as a percentage based on the total weight of the emulsion. The total weight of the emulsion includes the weight of the aqueous medium. Preferably, that sum is 0.5% or more; more preferably 1% or more; more preferably 2% or more; more preferably 3% or more. Preferably, that sum is 10% or less; more preferably 8% or less; more preferably 6% or less.

In the emulsion of the present invention, it is useful to characterize the ratio X:Y, where X is the weight of polyisocyanate (a) plus the weight of compound (b), and Y is the weight of compound (c). Preferably, X:Y is 0.1:1 or higher; more preferably 0.2:1 or higher; more preferably 0.5:1 or higher. Preferably, X:Y is 5:1 or lower; more preferably 2:1 or lower.

If a solvent other than water is present in an emulsion of the present invention, the preferred amount of solvent is, by weight based on the weight of the emulsion, 1% or less; more preferably 0.5% or less; more preferably 0.2% or less. If polyisocyanate (a) is ADI, the preferred amount of solvent in the emulsion is, by weight based on the weight of the emulsion, 0.02% or more; more preferably 0.05% or more. If polyisocyanate (a) is HDI, the preferred amount of solvent is, by weight based on the weight of the emulsion, 0.005% or less; more preferably 0%.

It is sometimes useful, prior to making the emulsion that contains compound (c), to make the mixture of polyisocyanate (a) and compound (b) as described in the first aspect of the present invention, without including any compound (c). When a composition containing 4 parts by weight of such a mixture and 96 parts by weight of water, at 25° C., particles suspended in an aqueous medium will preferably form, and preferably the D50 of the particles is 10 nm or larger. Preferably, such particles will have D50 of 1,000 nm or smaller; more preferably 500 nm or smaller; more preferably 300 nm or smaller.

The following are examples of the present invention.

The following Carbowax™ MPEG polymers (from the Dow Chemical Company) were used. Each has the structure $CH_3$—$(OCH_2CH_2)_n$—OH.

| Abbreviation | average n |
| --- | --- |
| MPEG 350 | 7.2 |
| MPEG 550 | 11.8 |
| MPEG 750 | 16.3 |
| MPEG 1000 | 22 |
| MPEG 2000 | 44 |

Emulsion particle sizes were measured by 90Plus Particle Size Analyzer from Brookhaven Instruments.

COMPARATIVE EXAMPLE 1: ETHOXYLATED HDI

HDI was mixed with one of the MPEG polymers as listed below. Each reaction mixture, prior to the reaction taking place, is characterized by the ratio of moles of isocyanate groups to moles of hydroxyl groups. The reaction mixture was held under nitrogen and stirred at 100° C. for five hours. It is contemplated that the following product was formed:

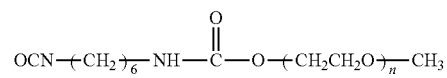

After the product was made, a mixture was made of the product and water, with 4 parts by weight product and 96 parts by weight water, and the particle size was measured. The results were as follows:

| Ethoxylated HDI in Water | | |
| --- | --- | --- |
| MPEG type | NCO:OH mole ratio | D50 (nm) |
| 750 | 2:1 | agglomerate |
| 550 | 2:1 | agglomerate |
| 550 | 6:1 | 6,414 nm |
| 350 | 2:1 | agglomerate |
| 350 | 5:1 | agglomerate |

None of the samples made an acceptable emulsion. It is contemplated that none of the samples would be useful as an emulsifier in a mixture with a compound (c).

COMPARATIVE EXAMPLE 2: ETHOXYLATED HDI DIMER

HDI dimer has the structure

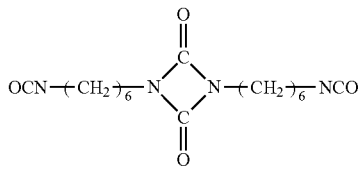

HDI dimer was mixed with one of the MPEG polymers as listed below. Each reaction mixture, prior to the reaction taking place, is characterized by the ratio of moles of isocyanate groups to moles of hydroxyl groups. The reaction mixture was held under nitrogen and stirred at 100° C. for five hours. It is contemplated that the following product was formed:

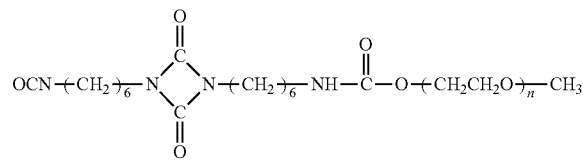

After the product was made, two mixtures were made as follows:

Mixture 2-1: 4 parts by weight of the product and 96 parts by weight of water,

Mixture 2-2: 2 parts by weight of the product; 2 parts by weight of HDI trimer, and 96 parts by weight of water, and the particle sizes were measured. The results were as follows:

| | HDI Trimer plus Ethoxylated HDI Dimer in Water | | |
|---|---|---|---|
| MPEG type | NCO:OH mole ratio | Mixture 2-1 D50 (nm) | Mixture 2-2 D50 (nm) |
| 750 | 2:1 | 14 | >1,000 |
| 550 | 6:1 | 163 | >1,000 |
| 550 | 5.4:1 | 68 | >1,000 |
| 550 | 3:1 | 21 | 1,074 |
| 550 | 2:1 | 15 | >1,000 |
| 350 | 6:1 | 114 | 560 |
| 350 | 3:1 | 86 | 8,284 |
| 350 | 2.5:1 | 35 | >1,000 |
| 350 | 2:1 | 25 | 1,105 |

It is desirable to make emulsion particles with an added crosslinker (in this case, HDI trimer) with D50 of 500 nm or less. None of the samples met this target. None of the samples would be useful as an emulsifier in a mixture with a compound (c).

EXAMPLE 3: ETHOXYLATED HDI TRIMER WITHOUT COMPOUND (C)

HDI trimer was mixed with one of the MPEG polymers as listed below. Each reaction mixture, prior to the reaction taking place, is characterized by the ratio of moles of isocyanate groups to moles of hydroxyl groups. The reaction mixture was held under nitrogen and stirred at 100° C. for five hours. It is contemplated that the reaction product included a compound having structure III where R is $-(CH_2)_6-$.

After the product was made, a mixture was made of the product and water, with 4 parts by weight product and 96 parts by weight water, and the particle size was measured. The results were as follows:

| Ethoxylated HDI Trimer in Water | | |
|---|---|---|
| MPEG type | NCO:OH mole ratio | D50 (nm) |
| 750 | 14:1 | 230 |
| 550 | 14:1 | 144 |
| 350 | 14:1 | 450 |
| 550 | 8:1 | 50 |
| 550 | 6:1 | 32 |
| 550 | 4:1 | dissolved |
| 550 | 2:1 | agglomerated |

EXAMPLE 4: ETHOXYLATED HDI TRIMER WITH COMPOUND (C)

Reaction products of HDI trimer and MPEG 550, at NCO:OH mole ratio of 6:1, were made as in Example 3. Mixtures were made with various additional compounds, as follows:

| Abbreviation | Compound | Supplier |
|---|---|---|
| Epoxy | D.E.R. ™ 331 ™ liquid epoxy resin | The Dow Chemical Co. |
| MDI-L | Isonate ™ 50 OP isocyanate; liquid; 50% 4,4' MDI and 50% 2,4' MDI | The Dow Chemical Co. |
| MDI-S | Isonate ™ 125M isocyanate; solid; 98% 4,4' MDI and 2% 2,4' MDI | The Dow Chemical Co. |

Each mixture contained 96 parts by weight of water, X parts by weight of reaction product (of the reaction between HDI trimer and MPEG), and Y parts by weight of additional compound, where X+Y equaled 4 parts by weight. The ratio X:Y is shown below. The particle sizes of the mixtures were measured with the results as follows:

| additional compound | X:Y | D50 (nm) |
|---|---|---|
| MDI-L | 0.5:1 | 130 |
| MDI-S | 0.5:1 | 162 |
| Epoxy | 0.5:1 | 125 |
| Epoxy | 0.75:1 | 145 |
| Epoxy | 1.0:1 | 266 |
| Epoxy | 1.5:1 | 1,186 |

The reaction product of HDI trimer with MPEG 550 at NCO:OH mole ratio of 6:1 acts as an useful emulsifier for a variety of additional compounds. Also, it is possible to vary D50 by varying the ratio X:Y.

EXAMPLE 5: ETHOXYLATED ADI TRIMER

ADI trimer was mixed with an MPEG compound and butyl acetate and held with stirring under nitrogen at 100° C. for 4 hours. The amount of butyl acetate was 30% by weight based on the weight of the total mixture. The amount of ADI trimer plus the amount of MPEG compound was 70% by weight based on the weight of the total mixture. It is contemplated that the reaction product included a compound having structure III where R is

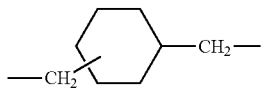

It is contemplated that a mixture of isomers was present.

Reaction products were mixed with water in the proportion of 4 parts by weight reaction product and 96 parts by weight water. Where an emulsion resulted, the particle size was measured. The results were as follows. "nt" means not tested.

Emulsion Formation of Ethoxylated ADI Trimer Compounds
(Emulsion formation = "yes", lack of emulsion = "fail")

| Mole Ratio NCO:OH | MPEG 550 | MPEG 750 | MPEG 1000 | MPEG 2000 |
|---|---|---|---|---|
| 10:1 | 192 | 112 | 89 | 111 |
| 12:1 | agglomerate | nt | nt | nt |
| 14:1 | nt | 160 | 153 | nt |
| 15:1 | nt | nt | 156 | nt |
| 18:1 | nt | 227 | 187 | 250 |
| 20:1 | nt | agglomerate | nt | agglomerate |
| 25:1 | nt | nt | 237 | fail |
| 30:1 | nt | nt | 272 | nt |
| 35:1 | nt | nt | agglomerate | nt |

All of the reaction products showed some ability to form an emulsion in water. The products made with MPEG 1000 showed the best ability to form an emulsion. It is contemplated that useful reaction products of ADI trimer with MPEG compounds could be made at mole ratio of NCO:OH below 10:1.

The invention claimed is:

1. An emulsion comprising particles suspended in an aqueous medium, wherein said particles comprise
   (a) one or more compound having structure A-NCO;
   (b) one or more compound having the structure of formula II:

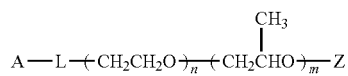

wherein A is the same as in compound (a), and
   (c) one or more water-insoluble compound
      that is different from compound (b);
      that does not have the structure A-NCO, wherein A is the same as in formula II; and
      that is selected from the group consisting of polyepoxy compounds and aromatic polyisocyanates;
   wherein
      A is a residue of a polyisocyanate,
      L is a linking group formed by a reaction of an isocyanate group with an isocyanate-reactive group,
      n is 5 to 25,
      m is 0 to 100, and
      Z is methyl or ethyl or propyl, and
   wherein the ratio of the sum of the moles of isocyanate groups on said compound (a) plus the moles of isocyanate groups on said compound (b) plus the moles of said L groups to the moles of said Z groups is 5:1 to 30:1.

2. The emulsion of claim 1, wherein m is zero.

3. The emulsion of claim 2, wherein A is the residue of a monomer of a diisocyanate, the residue of a dimer of a diisocyanate, or the residue of a trimer of a diisocyanate.

4. The emulsion of claim 3, wherein A is the residue of a trimer of a diisocyanate.

5. The emulsion of claim 4 wherein A is a residue of a trimer of hexane diisocyanate.

6. The emulsion of claim 4 wherein n is 10 to 14.

7. The emulsion of claim 1 wherein said water-insoluble compound (c) is an aromatic polyisocyanate.

8. The emulsion of claim 2, wherein A is the residue of a monomer of an aliphatic diisocyanate, the residue of a dimer of an aliphatic diisocyanate, or the residue of a trimer of an aliphatic diisocyanate.

9. The emulsion of claim 3, wherein A is the residue of a trimer of an aliphatic diisocyanate.

* * * * *